Figure 1:
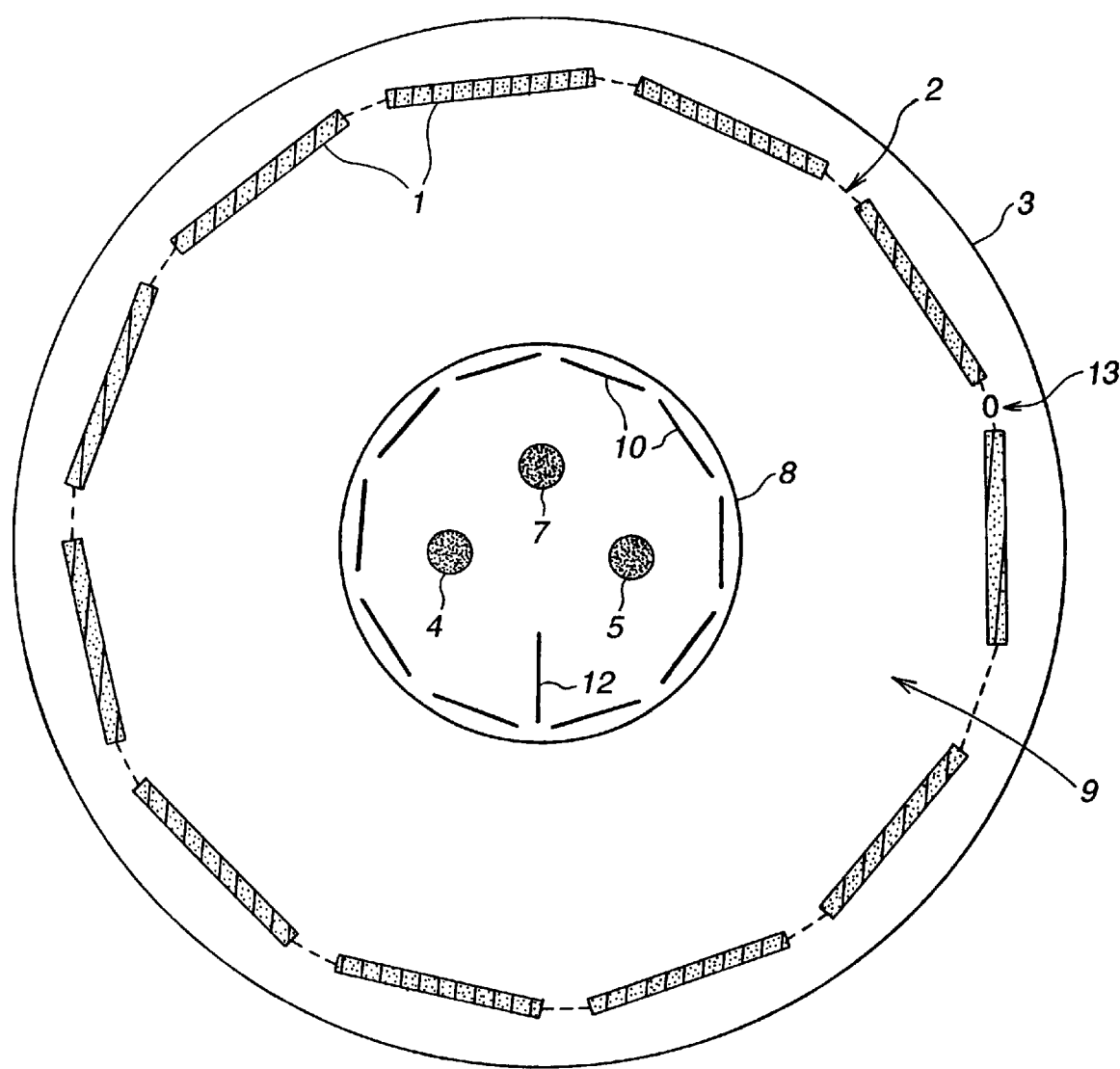

United States Patent [19]
Heeger et al.

[11] Patent Number: 5,898,816
[45] Date of Patent: Apr. 27, 1999

[54] METHOD FOR TREATING MATERIAL SAMPLES AND APPARATUS FOR TESTING EXPOSURE TO LIGHT AND WEATHERING

[75] Inventors: Roland Heeger, Bruchkobel; Arthur Schönlein, Russelsheim; Bernd Rudolph, Alzenau; Peter March, Frankfurt, all of Germany

[73] Assignee: Xenotest Gesellschaft für die Herstellung von Materialprüfgeräten mbH, Hanau, Germany

[21] Appl. No.: 08/983,390

[22] PCT Filed: Jul. 19, 1996

[86] PCT No.: PCT/EP96/03183

§ 371 Date: Jan. 19, 1998

§ 102(e) Date: Jan. 19, 1998

[87] PCT Pub. No.: WO97/04298

PCT Pub. Date: Feb. 6, 1997

[30] Foreign Application Priority Data

Jul. 20, 1995 [DE] Germany ............... 195 26 368

[51] Int. Cl.⁶ .................... F21V 9/00; G01N 17/00
[52] U.S. Cl. ................... 392/408; 73/86; 73/87; 73/150 R
[58] Field of Search ................... 392/480, 411, 392/407; 73/86, 87, 150 R

[56] References Cited

U.S. PATENT DOCUMENTS

| | | | |
|---|---|---|---|
| 3,224,266 | 12/1965 | Klippert | 73/150 R |
| 4,391,522 | 7/1983 | Schmid et al. | 73/150 R |
| 4,644,166 | 2/1987 | Sturm et al. | 73/150 R |
| 5,220,840 | 6/1993 | Neigoff et al. | |
| 5,226,318 | 7/1993 | Huber et al. | 73/159 |
| 5,421,198 | 6/1995 | More, III et al. | 73/170.15 |

FOREIGN PATENT DOCUMENTS

| | | |
|---|---|---|
| 03 02 986 A2 | of 0000 | European Pat. Off. |
| 01 83 921 | 6/1986 | European Pat. Off. |
| 03 20 209 A2 | 6/1989 | European Pat. Off. |
| 33 10 631 C2 | of 0000 | Germany |
| 20 14 288 | 10/1971 | Germany |
| 28 16 548 A1 | 10/1979 | Germany |
| 37 26 803 | 9/1988 | Germany |
| U 91 00 816 | 5/1991 | Germany |
| A57-021458 | 4/1982 | Japan |

*Primary Examiner*—Teresa Walberg
*Assistant Examiner*—Vinod D Patel
*Attorney, Agent, or Firm*—Frishauf, Holtz, Goodman, Langer & Chick, P.C.

[57] ABSTRACT

The invention concerns the ageing of material samples in the test enclosure of an apparatus for testing exposure to light and weathering, using visible light, UV light and medium- or long-wavelength IR radiation and with air circulation. In order to ensure reproducible test results, a value representing the surface temperature of the sample is measured by means of a temperature sensor and compared, at the input of a control unit, with a predefined reference temperature. In the event of a temperature difference, a control signal generated by the control unit adjusts the power supply to a separate IR radiant heater for medium- and long-wavelength IR radiation in such a way that the difference disappears in accordance with a predefined indicial response.

9 Claims, 3 Drawing Sheets

METHOD FOR TREATING MATERIAL SAMPLES AND APPARATUS FOR TESTING EXPOSURE TO LIGHT AND WEATHERING

The invention relates to methods for regulating the temperature of material samples in a light and weathering test apparatus with a closed-off chamber for samples, in which by means of a radiation arrangement visible light, UV and IR radiation is generated, and to a light and weathering test apparatus.

From German Patent DE 20 14 288, a light and weathering fastness testing apparatus with a sample chamber is known, in which samples located on a cylinder jacket surround a radiation source, and between this source and the samples a cylindrical mirror that selectively reflects the infrared component of the radiation and is permeable to the visible and UV components is provided; the effect of radiation in the short-wave infrared range from 800 to 1000 nm is considered especially problematic. Located in the middle of the cylindrical mirror is a metal tube through which a coolant flows, so that the intensity of the infrared radiation, simultaneously produced and occurring in the form of heat, which intensity grows with the intensity of the UV radiation can be dissipated; in this way, influence on the samples by breakdown reactions resulting from infrared radiation are largely avoided, so that any changes in the sample can be ascribed solely to the effect of UV radiation.

From European Patent Disclosure EP 0 320 209 A1, a weathering test system is also known in which the inside surfaces of samples are located on the inside of an approximately spherically formed mounting stand and exposed to an airstream, passed through it by a blower, and to a light source; with the aid of a regulating device for the blower, a predetermined temperature is maintained in the interior of the sample stand.

Moreover, from German Patent Disclosure DT 24 23 052 A1, a method and an apparatus for testing the weather resistance of samples is known in which for speeding up the testing of the samples, an artificial optical irradiation from one or more radiation sources, which also output ultraviolet or superactinic radiation is provided during twilight, darkness and nighttime; the test stand provided for testing weather resistance of samples in the open air has a sample carrier or a plurality of carriers for the radiation device with a guide and drive device; the radiation sources also output ultraviolet or superactinic radiation, and during the artificial irradiation at night no abnormally elevated temperatures. are attained, since high sample temperatures can cause a different kind of change to the bodies of the samples from that caused in natural weathering in the open air.

It proves to be a problem in the prior art that exact definition of the surface temperature, which should be kept as constant as possible if the samples are to be irradiated in a manner approximating actuality, cannot be performed here. In particular it is not possible for the black standard temperature, measured by a black standard thermometer, to be adjusted independently of other parameters and hence it is not possible to characterize temperature conditions of dark-colored sample bodies with low heat conductivity in the plane of the sample mounts during irradiation in accordance with DIN Standard 53387.

The object of the invention is thus to disclose a method for adjusting or keeping constant the surface temperature of the material samples and an apparatus for testing light and weather fastness having a sample chamber, in which the samples have an adjustable, optionally constant surface temperature which is independent of the intensity of the UV radiation, and in which the sample chamber temperature and atmospheric air circulation or climate control fan speed are kept constant; by means of filters, a radiation is to be output into the sample chamber that approximates global radiation, as disclosed for instance in the publication of the Commission International de l'Eclairage [International Lighting Commission] Publ. No. CIE85/1989, First Edition 1989, Table 4.

This object is attained in terms of the method by the characteristics of the body of claim 1.

In an advantageous feature of the method, the intensity of the IR radiation is regulated by comparison of a surface temperature measured in the region of the sample with a predetermined set-point temperature value, and the intensity of the IR radiation is controlled by a control signal of the regulator that depends on the difference or control deviation, ascertained at the regulator input, of the sensor signal from the set-point value signal.

The relatively simple regulation of the surface temperature of the samples as an individual parameter proves to be advantageous.

In terms of the apparatus, the object is attained by the characteristics of the body of claim 3.

In an advantageous feature of the apparatus, the radiation arrangement has at least one discharge lamp for emitting UV radiation and visible light as well as a separate temperature radiator as a source of infrared radiation; the intensity of the IR radiation output by the temperature radiator is adjusted by triggering the current supply by means of a control signal of the regulator, or the control deviation is adjusted; by means of interference filters, IR radiation below a wavelength of 1200 nm is absorbed or reflected, so that the IR radiation relevant to the heating of the surfaces of the samples has a wavelength of more than 1200 nm. An air stream with an approximately constant air throughput flows through the sample chamber by means of a blower.

Further advantageous features of the invention are disclosed in claims 5–13.

One substantial advantage is considered to be the always-constant surface temperature, because replicable test results can thus be attained; it also proves to be advantageous that a variation of the surface temperature can be performed purposefully by regulating the timing.

The subject of the invention will be described in further detail below in conjunction with FIGS. 1, 2 and 3.

Figure 2:
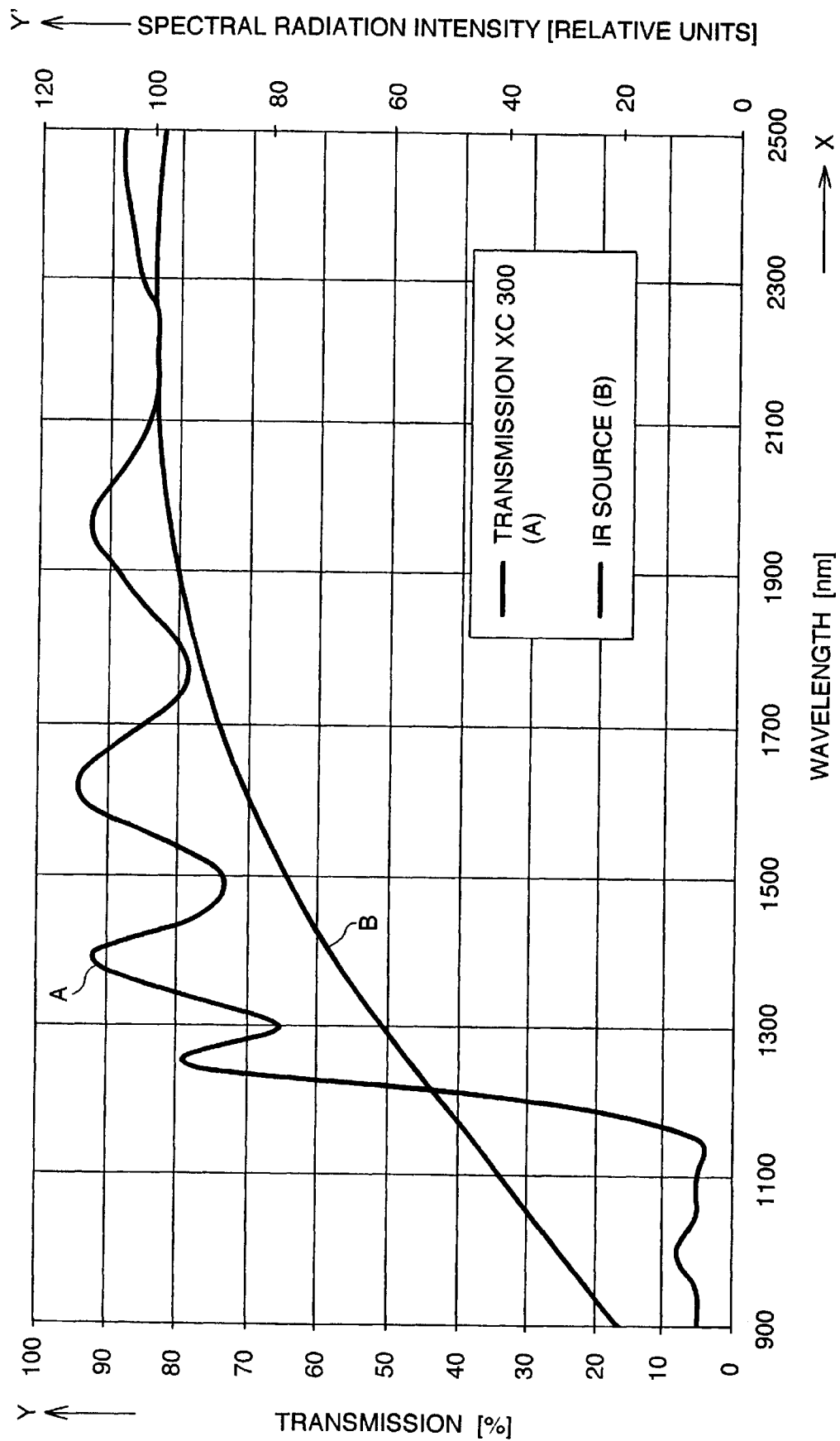
Figure 3:
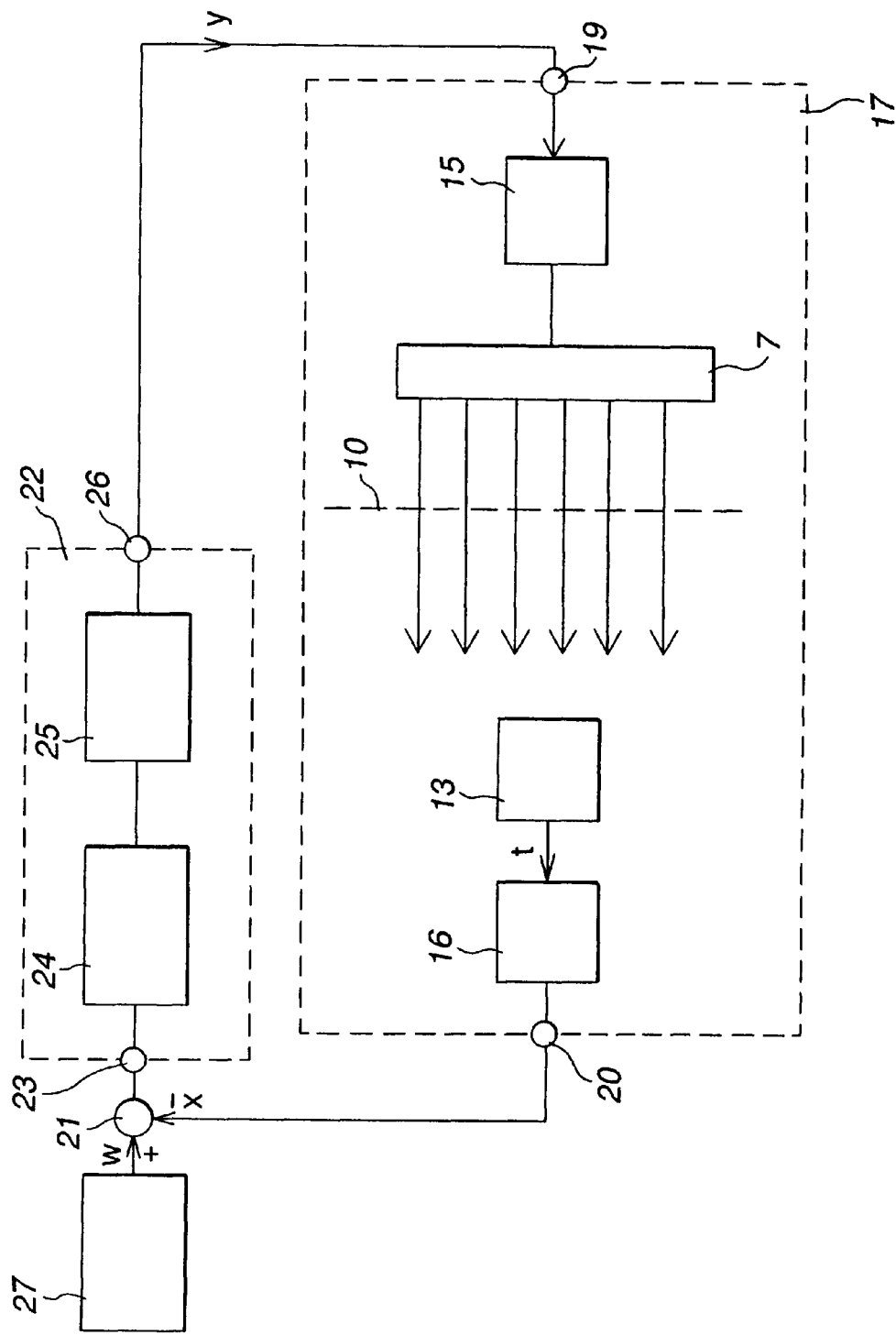

FIG. 1 schematically shows a cross section through the light and weathering test apparatus;

FIG. 2 shows the transmission of the filter characteristics and the spectral irradiation intensity of the infrared radiation source in the spectral range from 900 to 2500 nm;

FIG. 3 schematically, in the form of a block circuit diagram, shows the regulator for the light and weathering test apparatus.

As seen in a schematic cross-sectional view of the sample chamber in FIG. 1, the samples 1 are secured to a rotatable sample carrier 2, which is set into constant rotation by means of a drive device, not shown here. Located in the central region of the cylindrical housing 3 is a radiation arrangement comprising two discharge lamps 4, 5, for generating UV radiation and visible light, and one infrared radiator 7; the discharge lamps and the infrared radiator are closed off from the sample chamber 9 by a cylindrical filter 8, through which a coolant flows along the radiation passage faces and which in particular absorbs the short-wave infrared components of the discharge lamps in the range from 800 to 1000 nm, but at the same time is largely permeable to radiation in the long-wave ultraviolet range from 300 to 400 nm and in the visible spectral range. The inside surface of the filter 8 is also covered from the radiators or discharge lamps with interference filters 10 fitted against one another in the manner of a polygon, which are largely permeable to the long-wave UV range from 300 to 400 nm and the visible spectral range, while they largely absorb radiation in the infrared wavelength range from 900 to approximately 1200 nm. From a wavelength of approximately 1200 to 1250 on into the range of 2500 nm, the interference filters 10 are largely permeable to the medium- and long-wave infrared radiation, with a transmission of 70 to 95%.

In the interior of the filter 8, a body 12 is provided which absorbs the reflected infrared radiation and through which a coolant, such as air or water, flows for the sake of heat dissipation.

In the region of the rotatable sample carrier 2, a temperature sensor 13 is located at the level of the surfaces of the samples 1; it measures the heat of radiation transmitted as a result of the infrared radiation of the IR radiator 7, or in other words measures the surface temperature of the samples. With the aid of the regulating device described below, it is thus possible to adjust and regulate the black standard temperature of the substances to be tested, on the basis of the sample chamber temperature of the temperature dependent on the medium flowing around it, as one of the decisive parameters independently of other parameters; the tolerances specified in DIN 75220 with regard to global radiation, given in the aforementioned Table 4 of the CIE, should if at all possible be adhered to.

During normal operation it is possible to expose the samples to the relevant atmosphere for later use that flows through the sample chamber, such as air with a predetermined moisture content and a predetermined flow speed.

The filter characteristic of the interference filters 10 of FIG. 1 will now be described in detail, referring to curve A in FIG. 2. As can be seen from the wavelength plotted along the X axis, the transmission given along the Y axis, in the range up to about 1130 nm, is only 5%, while in the range beyond 1250 nm it rises to a range of 70 or more than 90%, so that the infrared spectrum, which impedes the process of testing the samples, is kept away from them, while the relatively low-energy infrared radiation of the medium- and longer-wave range reaches samples and can be adjusted or regulated in the form of independent parameters. Heat reflection filters with a blocking range from about 800 to 1200 nm, which are available on the market, have proved especially suitable as interference filters. It is also possible, however, to use other filters with an appropriate transmission characteristic.

Characteristic curve B in the graph in FIG. 2 is oriented to the spectral radiation intensity in relative units of the infrared radiation source 7, which is plotted along the Y' axis as a function of the wavelength given on the X axis; as can be seen from the course of curve B, the radiated intensity in the range from 900 to 1280 nm, is less than 60 relative units of the spectral radiation intensity, while in the range from 1300 to 2500 nm it rises from a value of 60 to a value of 100 pertaining to the relative radiation intensity, so that the spectral range relevant to the black standard temperature can be transmitted with a high intensity to the plane of the samples.

The regulating device will be described in further detail in terms of the schematic illustration in FIG. 3; together with the temperature sensor 13 and an analog/digital converter 16, the infrared radiator 7 supplied by a controllable power supply 15 forms the controlled path 17 of the regulating device. Via the input 19, by means of a control signal Y, the power supply 15 is triggered in such a way that a predetermined radiation intensity of the connected infrared radiator 7 can be attained by means of regulation. A radiator with a tungsten incandescent coil, with a power takeup in the range from 500 W to 2 kW, has proven especially suitable as the infrared radiator. The infrared radiation output by the radiator 7 to the sample chamber via infrared filters 10 generates a heat in the plane of the samples whose temperature is ascertained by the temperature sensor 13 and sent on in the form of an electrical signal t to the analog/digital converter 16; this latter element converts the analog signal t into a digital controlled variable x, which is delivered via the output 20 to a comparator 21 at the input 23 of the regulator 22; while the controlled variable x is delivered for instance as a negative digital signal, a predetermined digital set-point value w from a set-point value specifying device 27 is delivered in the form of a positive digital value to the comparator 21, and the digital control deviation (w–x) is thus ascertained at the output of the comparator and delivered to the regulator 22 via its input 23. A microprocessor 24 and a signal processor 25 are located inside the regulator 22, and as a result, a control signal y is generated at the output 26 of the regulator; it is used to control the power supply 15 for the infrared radiator 7 via the input 19 and is effective as a control signal until such time as the control deviation becomes w –x=0, and thus the radiation 7 output by infrared radiators corresponds to the specified set-point value w. Because of the digital design of the regulator 22, it is possible by programming the microprocessor as a closed-loop control component to attain an optimal closed-loop control behavior.

If the surface temperature of the specimens is to be varied during the treatment process, then it is possible instead of a fixedly predetermined set-point value w to use a timing transducer with a chronologically varied set-point value or with program regulation.

The use of an additional infrared radiator as a pure heat source according to the invention makes it possible for the surface temperature of the samples, which otherwise depends on the absorption behavior of materials to be tested, on the sample chamber temperature, and on the speed of the medium flowing through, to be adjusted and regulated fully independently as one of the decisive parameters.

We claim:

1. A method for regulating the temperature of material samples in a light and weathering test apparatus with a closed chamber with air circulation for material samples, in which chamber by means of a radiation arrangement, which includes at least one discharge lamp embodied as a xenon radiator, visible light, UV and IR radiation are generated, characterized in that the IR radiation is generated by a temperature radiator;

infrared radiation with a wavelength below 1200 nm is largely suppressed by means of filters;

IR radiation with a wavelength above 1200 nm is transmitted to the material samples;

the heat produced on the surfaces of the sample by the IR radiation is measured by means of temperatures as a temperature signal and supplied to a regulator for regulating the surface temperature to a predetermined set-point temperature value by controlling the intensity of the IR radiation;

and the radiation intensity of the temperature radiator is adjusted as a function of a control signal of the regulator, and the control signal is dependent on the control deviation between the set-point temperature value and the measured temperature signal.

2. A light and weathering test apparatus with a closed-off chamber for samples, in which a radiation arrangement surrounded by a rotatable sample holder is provided, which includes at least one discharge lamp formed as a xenon radiator and emitting both UV radiation and visible light and which radiates visible light and UV and IR radiation to the sample, characterized in that at least one temperature sensor (13) for regulating the intensity of the IR radiation is provided in the plane of the samples; and the radiation arrangement has at least one electric temperature radiator (7) for emitting IR radiation, whose intensity is adjustable by means of triggering its current supply via the control output (26) of a regulator (22), and the input (23) of the regulator is connected via a comparison element (21) to the temperature sensor (13) for the ascertaining the control deviation in the measured temperature value from a predetermined set-point temperature value signal.

3. The light and weathering test apparatus of claim 2, characterized in that at least one filter (10) for adapting the radiation output by the lamp to the global radiation is located between the sample chamber (9) and the discharge lamp.

4. The light and weathering test apparatus of claim 3, characterized in that the discharge lamp is surrounded, in the direction of the sample chamber (9), by a cylindrical filter (8) for absorbing the infrared components output by the discharge lamp (4, 5).

5. The light and weathering test apparatus of claim 2, characterized in that at least one filter (8, 10) for absorbing radiation with a wavelength below 1200 nm is located between the temperature radiator (7) and the sample chamber (9).

6. The light and weathering test apparatus of claim 5, characterized in that the temperature radiator, viewed in the direction of the sample chamber, is surrounded by at least one filter (8, 10) for absorbing radiation with a wavelength below 1200 nm.

7. The light and weathering test apparatus of claim 4, characterized in that the discharge lamp (4, 5) and temperature radiator (7) are located inside the cylinder filter (8).

8. The light and weathering test apparatus of claim 7, characterized in that at least the temperature radiator (7) is surrounded by flat filters (10) arranged in the manner of a polygon, for absorbing a wavelength below 1200 nm.

9. The light and weathering test apparatus of claim 2, characterized in that the temperature sensor (13) located in the plane of the samples is formed as part of a closed-loop control circuit which has a regulator (22) with comparison of the set-point and actual temperature values at the regulator input (23), and the regulator output (26) is connected to a final control element (15) for controlling the radiation output of the temperature radiator (7).

\* \* \* \* \*